(12) United States Patent
Hayden et al.

(10) Patent No.: US 6,295,859 B1
(45) Date of Patent: Oct. 2, 2001

(54) METHOD AND SYSTEM FOR REMOTELY DETERMINING COLUMN DENSITY OF TRACE GASES

(75) Inventors: Andreas F. Hayden, Sandy Hook; Robert J. Noll, Fairfield, both of CT (US)

(73) Assignee: The B. F. Goodrich Co., Charlotte, NC (US)

( * ) Notice: Subject to any disclaimer, the term of this patent is extended or adjusted under 35 U.S.C. 154(b) by 0 days.

(21) Appl. No.: 09/202,506
(22) PCT Filed: Apr. 17, 1998
(86) PCT No.: PCT/US98/07903
  § 371 Date: Sep. 7, 1999
  § 102(e) Date: Sep. 7, 1999
(87) PCT Pub. No.: WO98/48260
  PCT Pub. Date: Oct. 29, 1998

Related U.S. Application Data

(60) Provisional application No. 60/044,685, filed on Apr. 18, 1997.

(51) Int. Cl.[7] ................................................... G01N 21/35
(52) U.S. Cl. .................. 73/23.2; 73/23.28; 73/30.01; 250/339.07; 250/339.13
(58) Field of Search ............................. 73/23.2, 23.28, 73/30.01; 250/339.07, 339.13; 356/438

(56) References Cited

U.S. PATENT DOCUMENTS

| | | |
|---|---|---|
| 3,931,462 | 1/1976 | Exton . |
| 4,320,975 | 3/1982 | Lilienfeld . |
| 5,371,542 | 12/1994 | Pauli et al. . |
| 5,528,037 | 6/1996 | Whitsitt . |

FOREIGN PATENT DOCUMENTS 0 604 124  6/1994  (EP) .

OTHER PUBLICATIONS

Hayden, A., E. Niple, B. Boyce, "Determination of Trace--Gas Amounts in Plumes by the Use of Orthogonal Digital filtering of Thermal–Emission Spectra", Applied Optics, Jun. 1996.

*Primary Examiner*—Daniel S. Larkin
(74) *Attorney, Agent, or Firm*—James M. Rashid; Calfee, Halter & Griswold LLP

(57) ABSTRACT

An improved OBS based technique that monitors gas emissions from smoke stacks, tail pipes, and other sources, and that separates gas column density from thermal radiance contrast. The technique of the present invention utilizes a software generated digital filter (30) constructed to correlate with only the spectrum of gas (12) of interest, and have zero correlation with background components (22). Through using the improved OBS technique of the present invention, high performance and more positive cost effective gas monitoring systems and sensors may be built and implemented.

13 Claims, 3 Drawing Sheets

METHOD AND SYSTEM FOR REMOTELY DETERMINING COLUMN DENSITY OF TRACE GASES

CROSS-REFERENCE TO RELATED APPLICATION

This application is based upon and claims priority to United States Provisional Patent Application Ser. No. 60/044,685 filed Apr. 18, 1997 and entitled Remote Trace Gas Quantification Using Therma. IR Spectroscopy and Digital Filtering Based on Principal Components of Background Scene Clutter, the specification and drawings of which are herein expressly incorporated by reference.

BACKGROUND OF THE INVENTION

1. Technical Field

The present invention relates generally to digital filters, and more particularly to a method for detecting and monitoring atmospheric gases, such as gases emitted from smoke stacks or tail pipes, through use of a gas sensor and a digital filter constructed to correlate only with the spectrum of the gas of interest to yield the density of the gas.

2. Discussion

The detection and measurement of trace gases is often essential in order to adhere to environmental standards and regulations, or process control standards. As a result, there is a need by civilian and government agencies for a technique of passively detecting and measuring trace gases in a plume using target plume sensors. The sensors may be as close to an emissions source as the base of a smoke stack, or as far away as on an orbiting satellite.

One problem associated with detecting and measuring trace gases is that the spectral signal of interest associated with the trace gas is typically a small part of the overall signal measured by the sensor. It is often difficult for a basic correlation filter to detect this small target signal unless the background component of the measured spectrum is removed.

Several conventional spectral measurement techniques exist. One technique, known as two spectrum differencing, involves measuring a scene and subtracting the background spectrum from the target spectrum. However, the two pixel differencing does not eliminate spectrally correlated background features in a target spectrum, therefore leading to large errors in gas amount quantification, and leaving a large residual which masks the desired signal.

A second technique, known as model matching, takes a spectral measurement and generates a complex numerical model of the spectrum. The technique then adjusts model parameters until a spectral match is found. However, model matching techniques typically require long, complex computer runs that require a large amount of operator involvement to adjust the model parameters.

A third known technique is known as an orthogonal background suppression (OBS) technique. OBS techniques are used to measure the column density/thermal radiance contrast product of a gas plume using a passive thermal/infrared emission spectrometer. Column density refers to the number of molecules per unit area seen by the sensor, while thermal radiance contrast is the difference between the radiance of the scene behind a plume, and a Planck function generated with the temperature of the plume. Such a technique facilitates target signal detection in the presence of low signal to spectral clutter ratio. OBS techniques are based upon the assumption that background spectral clutter can be assumed to be a linear combination of background spectra taken with no target gas in the field of view. Such a technique finds the proper combination of background scene components and removes the components completely from the target spectrum, thereby leaving only the spectrum of the gas of interest, along with associated random noise.

One advantage of the OBS technique is that an optimal linear filter associated with the technique is able to suppress a large background component of a measurement, while yielding the column density thermal radiance contrast product (DCP) of a gas plume in the atmosphere. However, while present OBS techniques exhibit certain desirable results, the techniques are limited in effectiveness in that the techniques cannot separate the column density measurement from the thermal radiance contrast measurement.

Therefore, there is a need for an OBS based technique of passively detecting and measuring trace gases and a gas plume that allows the value of plume column density to be separated from the thermal radiance contrast.

SUMMARY OF THE INVENTION

Accordingly, the present invention provides an improved OBS based technique that monitors gas emissions from smoke stacks, tail pipes, and other sources, and that separates gas column density from thermal radiance contrast. The technique of the present invention utilizes software generated digital filter constructed to correlate with only the spectrum of gas of interest, and have zero correlation with background components. Through using the improved OBS technique of the present invention, high performance and more positive cost effective gas monitoring systems and sensors may be built and implemented.

More particularly, the present invention provides a method of measuring trace gases in a gas plume. The method comprises the steps of: detecting a target scene including gas plume information and background information; filtering the background information from the gas plume information to yield a density contrast product including both gas plume column density and gas plume thermal radiance contrast values; filtering the gas plume thermal radiance contrast value from the density contrast product to yield a gas plume column density estimate; and outputting the gas plume column density estimate for gas plume analysis purposes.

In addition, the present invention provides a system for measuring column density of a plume of gas. The system provides a sensor that measures target pixel information including background and gas plume information. A processor is connected to the sensor to store and process the target pixel information, and filter the background information from the target pixel information to yield a gas plume column density/thermal radiance contrast product. The processor also filters the gas plume column density/thermal radiance contrast product to separate the thermal radiance contrast from the gas plume column density to yield gas plume column density information. An output associated with the processor outputs the gas plume column density information from the processor for data analysis purposes.

DETAILED DESCRIPTION OF THE PREFERRED EMBODIMENT

Figure 1:
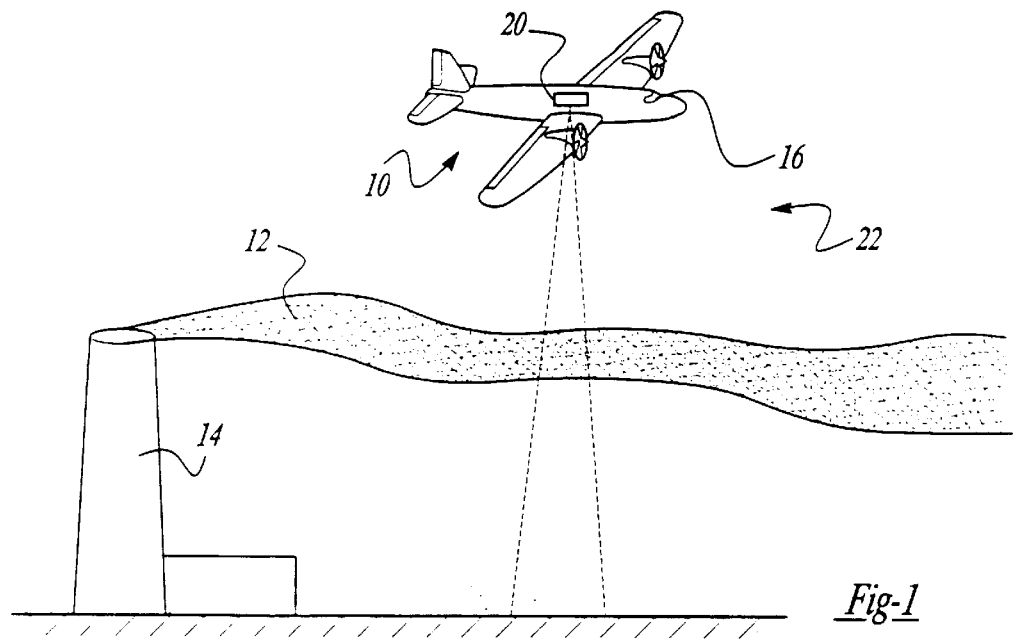
FIG. 1 is a schematic view of an environment in which the OBS gas measurement technique and system of the present invention is typically implemented.

Referring to FIG. 1, an OBS measurement system 10 according to the present invention is shown measuring a gas plume 12 emitted from a smokestack 14. The system 10 is installed in an airplane 16 for maintaining purposes so that a system sensor 20 is above the plume 12 looking down through it to the ground. The sensor 20 views the ground through intervening atmosphere 22 and through the plume 12. In a background pixel (not shown), the sensor views ground through intervening atmosphere only. The simulations and data discussed below are based on this geometry; however, it should be appreciated that the system may be implemented along a wide range of distances from the plume without affecting system results.

Figure 2:
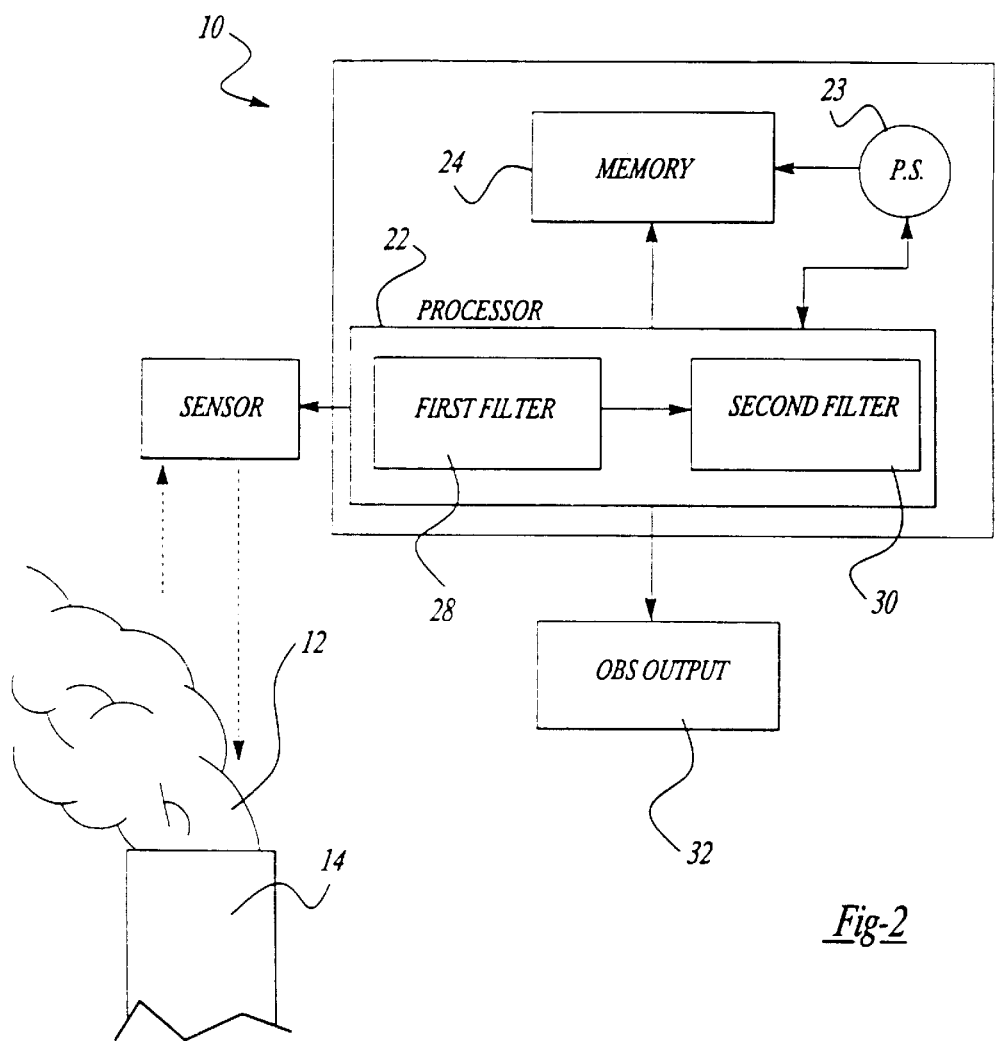
FIG. 2 is a block diagram of the system implementing the OBS measurement technique of the present invention.

FIG. 2 illustrates a preferred embodiment of the OBS system 10. Preferably, the system 10 is a conventional personal computer having an Intel® Pentium® 486 or higher processor. The system includes a processor 22 and associated power source 23 connected to the sensor 20. The processor 22 processes target pixel information measured by the sensor in accordance with the OBS technique of the present invention. The sensor shown is a JPL Airborne Emission Spectrometer. However, ground based sensors, such as the Hughes Mobile FTS ground spectrometer, may also be used. The OBS technique of the present invention is programmed into a computer memory 24 using conventional programming language such as C++, and generates digital filters 28, 30 based on pixel information measured by the sensor. As will be described in detail below, the digital filters produce a plume column density measurement that is separable from the plume radiance contrast, and output through system output 32 for plume analysis purposes.

Formulation of Original OBS Orthogonal Filter

The measured radiance in a target scene, or pixel, measured by the sensor 20 can be expressed as a sum of: background radiance transmitted through the atmosphere, background radiance transmitted through the plume and through the atmosphere, plume radiance transmitted through the atmosphere, and atmospheric radiance (Equation 1).

$$N_i^t = \underbrace{(1-f)N_i^g \tau_i^a}_{\substack{\text{background} \\ \text{(notpropogated} \\ \text{through plume)}}} + \underbrace{fN_i^g e^{-n_c \alpha_i} \tau_i^a}_{\substack{\text{background} \\ \text{(propogated} \\ \text{through plume)}}} + \underbrace{f(1-e^{-n_c \alpha_i})B_i(T_p)\tau_i^a}_{\substack{\text{plume} \\ \text{radiance}}} + \underbrace{N_i^a}_{\substack{\text{atmospheric} \\ \text{radiance}}}$$

Equation 1

In Equation 1, $N_i^t$ is the measured target radiance, f is the fraction of the pixel filled by the plume, $N_i^g$ is the radiance of the scene behind the plume, $t_i^a$ is the transmission of the atmosphere between the plume and the sensor, $n_c$ is the column density, $a_i$ is the absorption cross section of the molecule interest, B is the Planck function, $T_p$ is the plume temperature, and $N_i^a$ is the radiance of the atmosphere between the plume and the sensor. The subscript "i" indicates the quantities are arrays of values at varying wavenumber.

In conventional OBS techniques, the exponent terms (describing plume emissivity and plume transmittance) were expanded to first order (Equation 2).

$$e^{-n_c \alpha_i} \approx 1 - n_c \alpha_i$$

Equation 2

This truncated expansion implicitly assumes that the plume is optically thin and that higher order terms are negligible.

Rewriting Equation 1, using approximation 2, yields Equation 3.

$$N_i^t = f \Delta b_i n_c \alpha_i \tau_i^a + N_i^g \tau_i^a + N_i^a$$

Equation 3

$\Delta$ is the thermal radiance contrast (Equation 4).

$$\Delta b_i = B_i(T_p) - N_i^g$$

Equation 4

A more compact form of the equations is obtained if the spectra are expressed as n-dimensional vectors$_2$, where n is the number of wavelength samples in a spectrum. In vector notation, Equation 3 becomes Equation 5.

$$N^t = f n_c \alpha \tau^a \Delta b + N^g \tau^a + N^a$$

Equation 5

A conventional OBS technique assumes that the background components of the target signal, represented by the last two terms in equations 3 and 5, can be expressed as a linear combination of a set of measured background pixels. The following paragraphs describe how the correct linear combination of backgrounds is found.

A set of basis vectors spanning the set of measured background spectra can be constructed using singular value decomposition$_3$ (SVD) of the set of measured background spectra (Equation 6).

$$B = U \lambda V^T$$

Equation 6

B is the set of background spectra expressed as an array of vectors. U are the principal spectral components of the background set as found by SVD. $\lambda$ is the set of singular values describing the weights of the principal components. V is a "rotation matrix" describing how much of each principal component is in each background spectrum.

In the example application, the number of background spectra measured was fewer than the number of wavenumber samples in a spectrum. This does not lead to an underconstrained problem, however. It has been determined that for a wide variety of scenarios the number of non-noise basis vectors in the spanning set is fewer than the number of background spectra in the measured background set. SVD is able to separate random noise degrees of freedom from actual scene spectral clutter components.

Through tests conducted in the hyper to ultra spectral regimes (n>100 wavelengths), both uplooking and down looking, it has been determined that only on the order of ten principal components are needed to completely describe all the non-noise background variability. This statement holds true when background spectra are taken in close time and space to target spectra. The number of principal components required can be determined by looking at the singular values generated during SVD. After a certain number of principal components the singular values stop decreasing rapidly, indicating that all subsequent principal components are describing noise.

The OBS assumption, that the background radiance in a target pixel is a linear sum of measured background spectra, means that Equation 5 can be rewritten as Equation 7.

$$N^t = f n_c \alpha \tau^a \Delta b + Uc \quad \text{Equation 7}$$

Where the background terms of Equation 5 have been replaced by the linear sum of principal components, which are in turn a linear sum of the background spectra. The coefficient array c are the weights of the principal components describing the background in the target pixel. The orthonormality of U is used to find c and remove background components from the target spectrum.

The digital filter 28 can be constructed (Equation 8) such that its normalized dot product with $N^t$ yielded the $n_c \Delta b$ product (Equation 9).

$$(\alpha \tau \hat{a})^\perp \equiv m \alpha \tau - U[U'(\alpha \tau \hat{a})] \quad \text{Equation 8}$$

$$\frac{((\alpha \tau^{\hat{a}})^\perp)^T}{((\alpha \tau^{\hat{a}})^\perp)^T (\alpha \tau^{\hat{a}})} N^t = n_c \Delta b \equiv DCP \quad \text{Equation 9}$$

The superscript T indicates vector or matrix transpose. The atmospheric transmission, $\tau^{\hat{a}}$, used in constructing the filter in Equation 8, is an estimate based on knowledge of the atmospheric conditions during the measurements and is generated using the commercially available programming language FASCODE.

As discussed below, the OBS technique of the present invention is able to separate $n_c$ and $\Delta b$ by using higher order terms in exponent expansion.

Extension of OBS to Measure Absolute Column Density

If Equation 2 is completely expanded and combined with Equation 1, Equation 10 results:

$$N^t = f \Delta b \sum_{i=1}^{\infty} \left[ \frac{(-1)^{(i+1)} n_c^i \alpha^i \tau^a}{i!} \right] + Uc \quad \text{Equation 10}$$

Originally $\Delta b$ was treated as a constant. This worked for conventional OBS techniques. Simulations showed that for thick plumes there was coupling between higher order $\Delta$ terms and the $\Delta b$ spectrum which caused errors in $n_c$ determination. It was found that modeling $\Delta b$ as a linear function of wavenumber (Equation 11) allowed more accurate estimation of $n_c$.

$$\Delta b_i = \overline{\Delta b} + (\overline{v} - v_i) b \quad \text{Equation 11}$$

In Equation 11: $\overline{\Delta b}, \overline{v}$, b are constants and $v_i$ is the $i^{th}$ wavenumber. The average thermal radiance contrast term, $\overline{\Delta b}$, is the thermal contrast constant of original OBS. WO 98/48260 PCT£JS98/07903

Rewriting Equation 10, using Equation 11, yields Equation 12.

$$N^t = f \overline{\Delta b} \sum \left[ \frac{(-1)^{(i+1)} n_c^i \alpha^i \tau^a}{i!} \right] + \quad \text{Equation 12}$$

-continued $$f \overline{v} b \sum_{i=1}^{\infty} \left[ \frac{(-1)^{(i+1)} n_c^i \alpha^i \tau^a}{i!} \right] -$$

$$v b f \sum_{i=1}^{\infty} \left[ \frac{(-1)^{(i+1)} n_c^i \alpha^i \tau^a}{i!} \right] + Uc$$

By analogy to Equation 8 and 9, it would be desirable to create the filter 30 so that when applied to Equation 12 yields the coefficient of a particular $a_i$. In order to do this an augmented background B' needs to be constructed (see Equation 5) so that the basis set of vectors (U') spanning B' includes principal background components (U) as well as $(\alpha^j \tau^a)$, and $(v \, \alpha^j \tau^a)$ terms. Note that $j \neq i$.

A filter for the coefficients of the $\alpha_i$ term is generated using Equation 13.

$$(a^i \tau^{\hat{a}})^\perp \equiv a^i \tau^{\hat{a}} - U'[U'^T (a^i \tau^{\hat{a}})] \quad \text{Equation 13}$$

The filter (Equation 13) applied to Equation 12, yields Equation 14.

$$\frac{((\alpha^i \tau^{\hat{a}})^\perp)^T}{((\alpha^i \tau^{\hat{a}})^\perp)^T (\alpha^i \tau^{\hat{a}})} N^t = f \overline{\Delta b} (-1)^{(i+1)} \frac{n_c^i}{i!} + \quad \text{Equation 14}$$

$$f b \overline{v} \frac{(-1)^{(i+1)} n_c^i}{i!} - \frac{f b ((\alpha^i \tau^{\hat{a}})^T (v \alpha^i \tau^a))(-1)^{(i+1)} n_c^i}{((\alpha^i \tau^{\hat{a}})^\perp)^T (\alpha^i \tau^{\hat{a}}) i!}$$

Note that $(\alpha^i \tau \hat{a})\perp$ was constructed to cancel all $\alpha^j$ terms in the absorption cross section spectra with $j \neq i$. Also, assuming $\tau^{\hat{a}}$ is a good approximation for $\tau^a$ and noting that the magnitude of the last two terms in Equation 14 are nearly equal, yields Equation 15.

$$\frac{((\alpha \tau^{\hat{a}})^\perp)^T}{((\alpha \tau^{\hat{a}})^\perp)^T (\alpha \tau^{\hat{a}})} N^t \approx f \overline{\Delta b} (-1)^{(i+1)} \frac{n_c^i}{i!} \quad \text{Equation 15}$$

Filtering for the coefficient of a yields:

$$\frac{((\alpha \tau^{\hat{a}})^\perp)^T}{((\alpha \tau^{\hat{a}})^\perp)^T (\alpha \tau^{\hat{a}})} N^t = f \overline{\Delta b} n_c. \quad \text{Equation 16}$$

Equation 16 and 17 yield the conventional OBS result.

$$DCP_1 \equiv \frac{((\alpha^2 \tau^{\hat{a}})^\perp)^T}{((\alpha \tau^{\hat{a}})^\perp)^T (\alpha \tau^{\hat{a}})} N^t = f \overline{\Delta b} n_c \quad \text{Equation 17}$$

Filtering for the coefficient of $\alpha_2$ yields:

$$DCP_i \equiv \frac{((\alpha \tau^{\hat{a}})^\perp)^T}{((\alpha \tau^{\hat{a}})^\perp)^T (\alpha \tau^{\hat{a}})} N^t = f \overline{\Delta b} \frac{n_c^2}{2} \quad \text{Equation 18}$$

The filter 30, which provides an estimate for plume column density, is now simply generated by the following equation:

$$\hat{n}_c = -2 \frac{DCP_2}{DCP_1} \quad \text{Equation 19}$$

Note that $\hat{n}_c$ is a biased estimator for $n_c$ for at least two reasons:

1) Because of system noise (assumed to be gaussian, white, and spectrally uncorrelated). The filtered measurements $DCP_1$ and $DCP_2$ will have some mean and variance. Even though $DCP_2/DCP_1$ is not necessarily the ratio of the means of $DCP_1$ and $DCP_2$.

2) As described in more detail below, noise will "mask" higher order α terms.

An explicit noise term has been left out of the foregoing equations. When a spectrum is measured it will include the radiances described in Equation 1 plus a vector of random noise. It is assumed that noise in each wavenumber bin is zero mean, gaussian, uncorrelated, and has a standard deviation equal to noise equivalent spectral radiance (NESR). When the linear filters described in Equations 17 and 18 are applied to an ensemble of these random spectra the standard deviation of the results are the noise equivalent density contrast products, $NE_{DCP1}$ and $NE_{DCP2}$.

$$NE_{DCP1} = \frac{NESR}{(([(\alpha \tau^{\wedge a})^\perp))^T(\alpha \tau^{\wedge a})])^{\frac{1}{2}}} \quad \text{Equation 20}$$

$$NE_{DCP2} = \frac{NESR}{\left(([(\alpha^2 \tau^{\wedge a})^\perp))^T(\alpha^2 \tau^{\wedge a})]\right)^{\frac{1}{2}}}. \quad \text{Equation 21}$$

The noise equivalent $n_c$ ($NE_{nc}$) is the standard deviation of the ratio:

$$\hat{n}_c \pm NE_{nc} = -2 DCP_2 \pm \frac{NE_{DCP2}}{DCP_1 \pm NE_{DCP1}} \quad \text{Equation 22}$$

Therefore:

$$NE_{nc} = 2 \left[ \frac{(DCP_2 NE_{DCP1})^2}{DCP_1^4} + \frac{NE_{DCP2}^2}{DCP_1^2} \right]^{\frac{1}{2}} \quad \text{Equation 23}$$

The thermal radiance contrast can be estimated using $DCP_1$ and $DCP_2$ in a fashion similar to $n_c$ determination (Equation 24).

$$\overline{\Delta b} = -\frac{DCP_1^2}{2 \hat{f} DCP_2} \quad \text{Equation 24}$$

Where $\hat{f}$ is an estimate of the plume fill factor.

To get plume temperature from the thermal radiance contrast, we need an estimate of the ground radiance, $N^g$. Equation 25 can then be solved for $T_p$, (Equation 26).

$$\hat{\Delta b} = B_\nu) T_p) - \hat{N}_i^g \quad \text{Equation 25}$$

$$T_p = \frac{c_2 \overline{\nu}}{\ln\left(\frac{c_1 \overline{\nu}^3}{(\overline{\Delta b} + \hat{N}_i^g)} + 1\right)} \quad \text{Equation 26}$$

Where $B_\nu$ is the value of Planck's function at the spectral window's average wavelength, $$\overline{\hat{N}_i^g}$$

is the estimated average background radiance in the target pixel, $c_1$ and $c_2$ are the coefficients of Planck's equation.

Simulation Results

Figure 3:
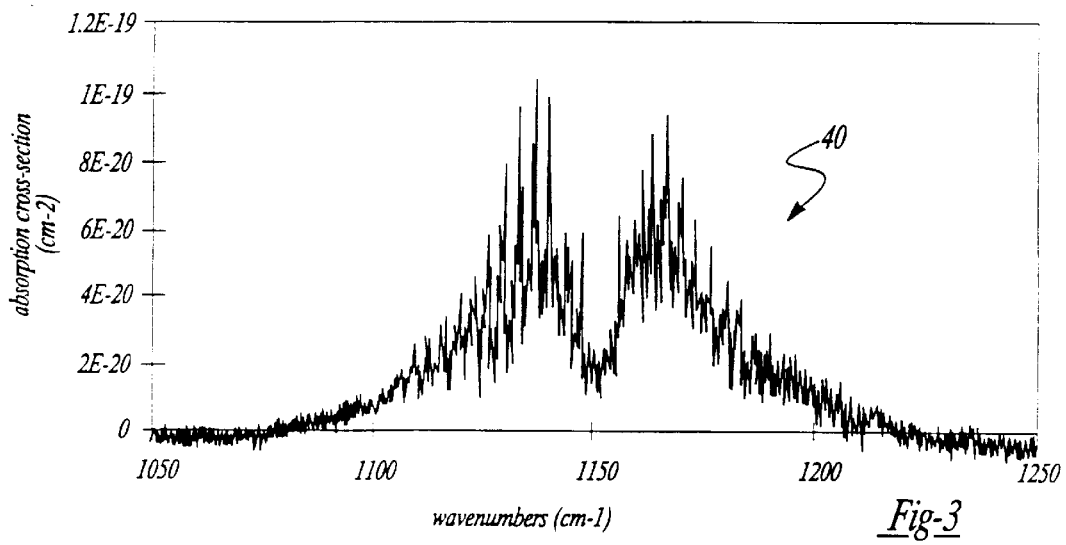
FIG. 3 graphically illustrates a simulated gas plume spectrum.

FIG. 3 shows a simulated $SO_2$ plume spectrum at 40. The OBS technique of the present invention is used to extract $n_c$ of $SO_2$ in this spectrum. The simulated $SO_2$ plume spectrum 40 is simulated downlooking from 4.5 km and includes: ground radiance, plume radiance and transmission atmospheric radiance and transmission, and white noise.

The parameters used to generate the spectrum shown in FIG. 3 are listed in Table 1:

TABLE 1

| | |
|---|---|
| $n_c$ of $SO_2$ | $1 \times 10^{19}$ molecule/cm$^{-2}$ |
| $T_p$ | 305 K |
| $T_g$ | 295 K |
| ground emissivity | 1 |
| fill factor | 1 |
| atmosphere model | mid-latitude winter |
| sensor altitude | 4.5 km (nadir view) |
| NESR | $1 \times 10^{-7}$ w/cm$^2$sr cm$^{-1}$ |

The backgrounds for the simulation where a set of black body spectra generated with ground temperature varying from 290K to 300K. The peak target signal to NESR ratio in the target pixel is ten. The peak target signal to scene clutter ratio is 1/7.

Figure 4:
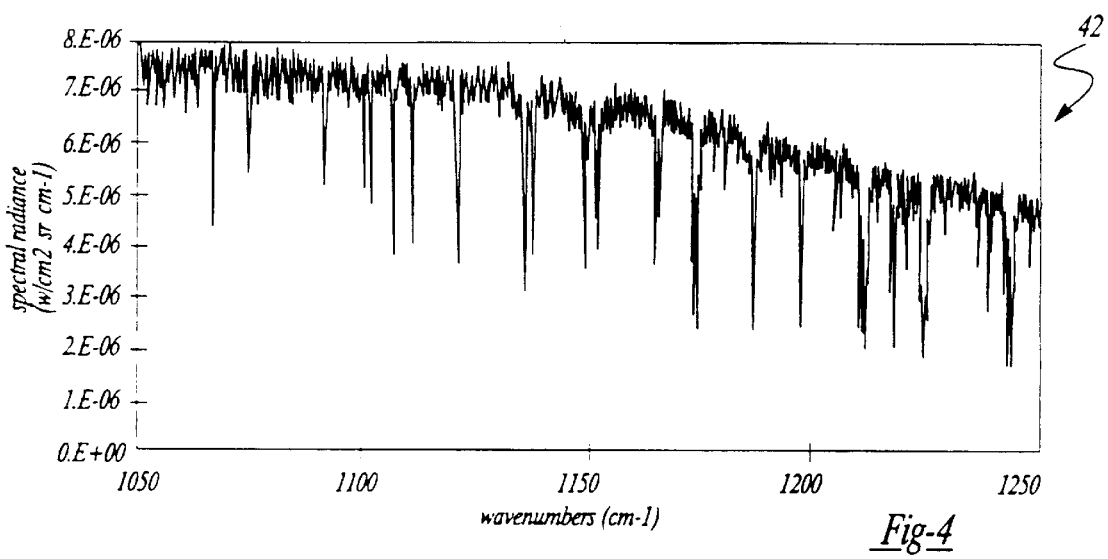
FIG. 4 graphically illustrates a molecular absorption cross section of the gas plume of FIG. 3 as used to construct a system filter.

FIG. 4 shows the molecular absorption cross-section of $SO_2$ used to construct the $SO_2$ filter at 42. Note that visually the $SO_2$ features are almost completely obscured by the spectral clutter in the target spectrum.

Figure 5:
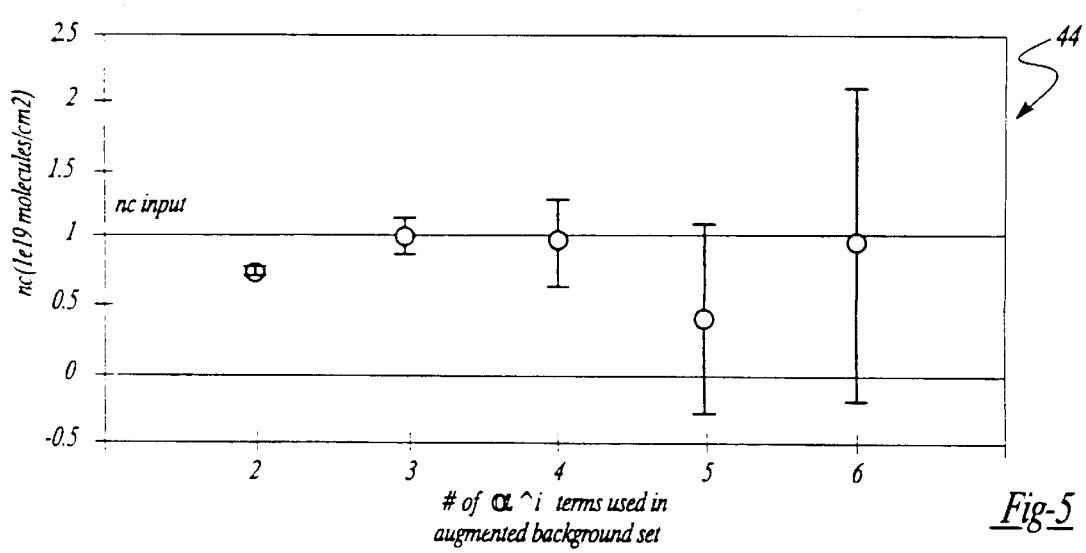
FIG. 5 is a graph of filter results for the simulated gas plume of FIG. 3.
Figure 6:
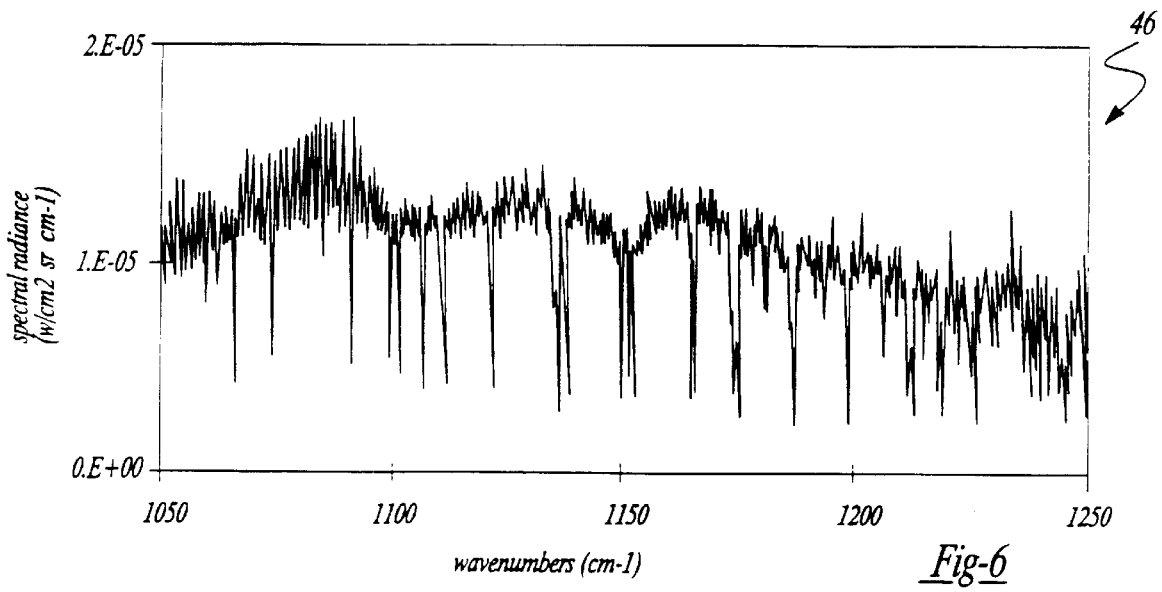
FIG. 6 is a graph of an example target spectrum generated from an actual field data.

FIG. 5 shows filter results for the simulated $SO_2$ plume at 44. The x-axis is number of $\alpha^i$ terms added to the augmented background set B'. For example, if the number of $\alpha^i$ terms indicated is two then B' includes: the non-noise background principal components, $(\alpha^2 \tau^a)$, and $(v \alpha^2 \tau^a)$. The error bars indicate the noise equivalent column density ($NE_{nc}$).

The estimated $n_c$ results (based on simulation) is plotted versus number of terms included in the augmented background set. Error bars indicate $NE_{nc}$. Amount of $SO_2$ in plume is indicated by the line "nc input".

The plot 44 in FIG. 5 starts with $\alpha^2$ added to B' since at least two terms are required in the expansion to determine $n_c$.

As the number of terms used to generate filter increases, the estimated value of nc approaches the input value. But, at the same time, noise equivalent $n_c$ ($NE_{nc}$) increases. There is a number of terms where the best estimate of $n_c$ is found. This estimate will be biased by the early cutoff of expansion terms.

Field Data Results

In the above example, data was taken with the JPL Airborne Emission Spectrometer (AES) of a plume from a smokestack. The altitude of the sensor was 15,000 feet and was nadir viewing. The data received was calibrated in units of watts/cm$^2$ sr cm$^{-1}$. The spectra was windowed to 1050–1250 cm$^{-1}$ since $SO_2$ measurements were desired.

The sensor is a linear array of four detectors which can be "push-broomed" to build a 4xm ultra-special image (m is the number of scans in a run). The sensor can also track a stationary target on the ground as the aircraft flies over. During scans one hundred nine the sensor was push-broomed across the ground leading up to the target smokestack. These thirty-six spectra comprised the original background set, B. During scans nine hundred twenty-eight the sensor locked on to the stack and viewed the plume from various angles as the aircraft flew over.

FIG. 5 shows a graph of smokestack spectral plume radiance generated from field data at 46. The emission feature between 1050 cm-1 and 1100 cm-1 is hot $CO_2$ which is also an effluent from the stack. If the $CO_2$ is not accounted for in constructing a filter for $SO_2$, the filter may couple with the $CO_2$ feature and give an incorrect $SO_2$ measurement result. To account for interferant gases (e.g., in this case, $CO_2$), the absorption spectrum of a suspected interferant is added to the augmented background set, B'. When a spectrum is added to B', the filter constructed from B' will not correlate with that spectrum. With $CO_2$ added to the B', the $CO_2$ emission will not interfere with the $SO_2$ measurement.

Figure 7:
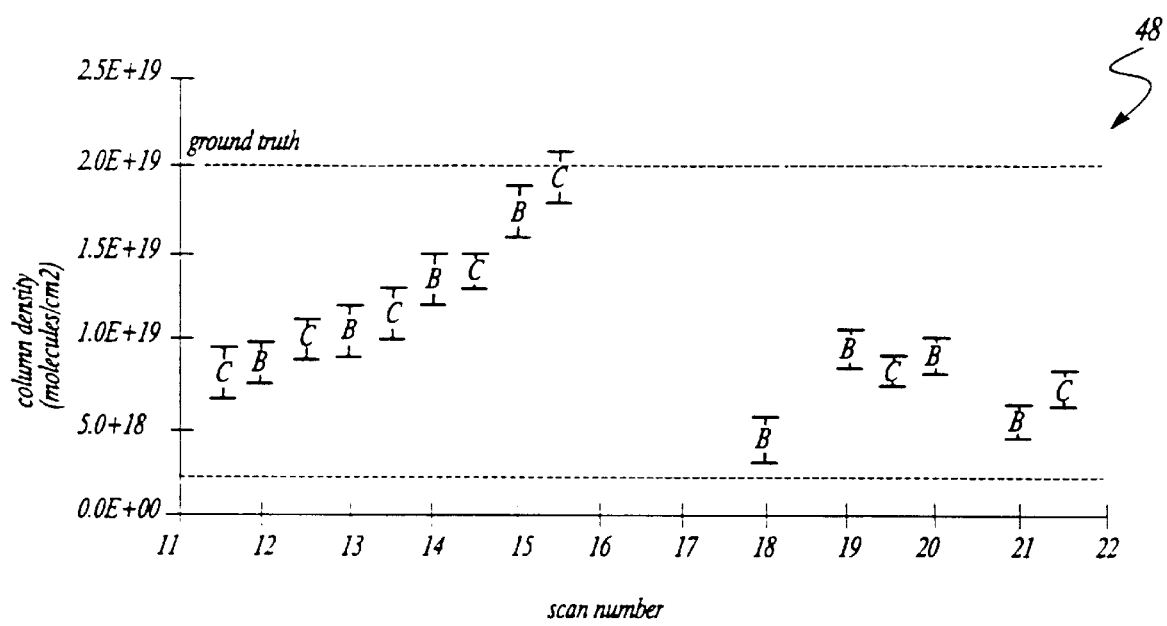
FIG. 7 is a graph of column density versus scan number for measured field data.

FIG. 7 shows $n_c$ estimates, calculated $NE_{nc}$, and ground truth estimates for $SO_2$ column density in the plume at 48. The error bars indicate only the $NE_{nc}$ and do not take into account any other possible systematic errors. The ground truth estimate range is indicated by the horizontal lines.

Scans one hundred nine where used as background so no $SO_2$ measurements are shown for them. In scans ten, and after twenty-one the plume was either too thin or the thermal contrast too low to be able to make column density measurements (even though for those scans $SO_2$ could be detected). In scans sixteen and seventeen the plume was being viewed against the hot roof of a building. In these two scans, the plume was about the same temperature as the background, so the thermal contrast was too low to make column density measurements.

Upon reading the foregoing description, it will be appreciated that the OBS technique of the present invention is a linear filtering technique based on the assumption that background scene components in a target pixel are a linear sum of measured scene background spectra. A linear filter is constructed to reject background scene components and yield plume gas column density-thermal radiance contrast products. If filters for various powers of target gas absorption spectra are constructed, absolute column density and plume temperature can be separately determined for plume analysis purposes.

Various other advantages of the present invention will become apparent to those skilled in the art after having the benefit of studying the foregoing text and drawings, taken in conjunction with the following claims.

What is claimed is:

1. A method of measuring trace gases in a gas plume, comprising the steps of:
   detecting a target scene including gas plume information and background information;
   filtering the background information from the gas plume information to yield a density contrast product including both gas plume column density and gas plume thermal radiance contrast values;
   filtering the gas plume thermal radiance contrast value from the density contrast product to yield a gas plume column density estimate; and
   outputting the gas plume column density estimate for gas plume analysis purposes.

2. The method of claim 1, further comprising the step of generating a noise equivalent spectral radiance value based on the step of filtering the background information from gas plume information and the step of filtering the gas plume thermal radiance contrast value from the density contrast product.

3. The method of claim 1, further comprising the steps of:
   measuring ground temperature during the step of detecting a target scene; and
   determining gas plume temperature based on the steps of measuring ground temperature, filtering the background information from the gas plume information, and filtering the gas plume thermal radiance contrast from the density contrast product.

4. The method of claim 3, wherein the step of measuring gas plume temperature is implemented by the following equation:

$$T_p = \frac{c_2 \bar{v}}{\ln\left(\frac{c_1 \bar{v}^3}{\left(\overline{\Delta b} + \overline{N}_i^g\right)} + 1\right)}$$

$$\overline{\Delta b} = B_v(T_p) - \overline{N}_i^g$$

where $B_v$ is the value of Planck's function at the spectral window's average wavelength, $$\overline{N}_i^g$$

is the estimated average background radiance in the target pixel, $c_1$ and $c_2$ are the coefficients of Planck's equation, and $\Delta b$ is the average gas plume thermal radiance contrast.

5. A method of determining column density of a gas plume, comprising the steps of:
   measuring target pixel information including background information, gas plume thermal radiance contrast information, and gas plume density information;
   filtering the background information and thermal radiance contrast information from the target pixel information to yield gas plume density information; and
   outputting the gas plume density information for gas plume analysis purposes.

6. The method of claim 5, wherein the step of filtering background information and thermal radiance contrast information from the target pixel information includes the step of modeling thermal radiance as a linear function of gas plume spectrum wave number.

7. The method of claim 5, further comprising the step of calculating a gas plume range of deviation associated with the gas plume density information; and
   outputting gas plume range of deviation information with the gas plume density information to account for pixel scene noise.

8. The method of claim 5, further comprising the step of calculating gas plume temperature information from the gas plume thermal radiance contrast information.

9. A system for measuring column density of a plume of gas, comprising:
   a sensor that measures target pixel information including background radiance, atmospheric radiance, and gas plume radiance;
   a processor connected to the sensor that stores and processes the target pixel information;
   a first filter generated by the processor that filters the background and atmospheric radiance from the target pixel information to yield a gas plume column density/thermal radiance contrast product;
   a second filter generated by the processor that filters the thermal radiance contrast from the column density/thermal radiance contrast product to yield gas plume column density information; and
   an output associated with the processor that outputs the gas plume column density information from the processor for data analysis purposes.

10. The system of claim 9, wherein the processor is operative to generate noise information that compensates for noise associated with the target pixel information.

11. The system of claim 9, wherein the processor is further operative to calculate gas plume temperature based on the thermal radiance contrast filtered by the second filter, and an estimate of ground radiance as sensed by the sensor.

12. A system for measuring column density of a plume of gas, comprising:

a sensor that measures target pixel information including background and gas plume information;

a processor connected to the sensor that stores and processes the target pixel information, and that filters the background information from the target pixel information to yield a gas plume column density/thermal radiance contrast product, said processor further filtering the gas plume column density/thermal radiance contrast product to separate the thermal radiance contrast from the gas plume column density to yield gas plume column density information; and an output associated with the processor that outputs the gas plume column density information from the processor for data analysis purposes.

13. The system of claim 12, wherein the processor generates a first digital filter to filter the background information from the target pixel information to yield a gas plume column density/thermal radiance contrast product, and a second digital filter to filter the gas plume column density/thermal radiance contrast product to separate the thermal radiance contrast from the gas plume column density to yield the gas plume column density information.

\* \* \* \* \*